(12) United States Patent
Eiff et al.

(10) Patent No.: US 7,855,354 B2
(45) Date of Patent: Dec. 21, 2010

(54) MEASURING DEVICE AND METHOD FOR THE 3D-MEASUREMENT OF DENTAL MODELS

(75) Inventors: Wolfgang Eiff, Heppenheim (DE); Peter Fornoff, Reichelsheim (DE)

(73) Assignee: Sirona Dental Systems GmbH, Benshiem (DE)

( * ) Notice: Subject to any disclaimer, the term of this patent is extended or adjusted under 35 U.S.C. 154(b) by 218 days.

(21) Appl. No.: 12/213,984

(22) Filed: Jun. 26, 2008

(65) Prior Publication Data

US 2009/0011386 A1  Jan. 8, 2009

(30) Foreign Application Priority Data

Jul. 2, 2007 (DE) .................. 10 2007 030 768

(51) Int. Cl.
*A61C 13/34* (2006.01)
(52) U.S. Cl. .............. 250/234; 356/601; 356/612; 433/29; 433/215
(58) Field of Classification Search ........... 50/234, 50/235; 356/601, 603, 612, 625; 433/29, 433/215
See application file for complete search history.

(56) References Cited

U.S. PATENT DOCUMENTS

| | | | |
|---|---|---|---|
| 5,369,490 A | 11/1994 | Kawai et al. | |
| 5,548,405 A | 8/1996 | Motosugi | |
| 6,287,121 B1 | 9/2001 | Guiot et al. | |
| 6,974,964 B1 | 12/2005 | Wang | |
| 7,006,210 B2 * | 2/2006 | Overbeck et al. | 356/138 |
| 7,209,228 B2 | 4/2007 | Li et al. | |
| 2004/0201856 A1 | 10/2004 | Quadling et al. | |
| 2005/0234344 A1 * | 10/2005 | Sanilevici et al. | 600/476 |
| 2006/0102833 A1 | 5/2006 | Eiff et al. | |

FOREIGN PATENT DOCUMENTS

| | | |
|---|---|---|
| EP | 0600800 | 6/1994 |
| EP | 1609437 | 12/2005 |

OTHER PUBLICATIONS

English Abstract of EP 0600800.

* cited by examiner

*Primary Examiner*—Seung C Sohn
(74) *Attorney, Agent, or Firm*—Dykema Gossett PLLC

(57) ABSTRACT

A scanning system for carrying out 3D scanning of dental models in a scanning direction V including a holding device for a whole jaw model which spans an occlusal plane E over a line-shaped mandibular arch, a base, a swivel bearing on a swivel axis normal to the scanning direction V and a stage mounted for rotation on the swivel bearing relatively to the base, on which the dental model to be scanned can be mounted. The stage can be rotated through an angular range δ of at least 150° about the swivel axis, and the whole jaw model can be mounted such that said occlusal plane E is aligned parallel to said scanning direction V. An evaluation unit receives data from a detector to generate a 3D data set.

14 Claims, 2 Drawing Sheets

MEASURING DEVICE AND METHOD FOR THE 3D-MEASUREMENT OF DENTAL MODELS

TECHNICAL FIELD

The present invention relates to a scanning system for carrying out three dimensional scanning of dental models in a scanning direction V, which scanning system comprises a holding device for a whole jaw model, which spans an occlusal plane E over a line-shaped dental arch or mandibular arch, and the scanning system further comprises a base, a swivel bearing extending normal to the scanning direction V, and a stage disposed such that it can swivel via the swivel bearing relatively to the base and on which the dental model to be scanned can be mounted.

The invention also relates to a scanning system for carrying out three dimensional scanning of dental models, which scanning system comprises a holding device for a whole jaw model, and a base, a swivel bearing, and a stage disposed such that it can swivel via the swivel bearing relatively to the base and on which the dental model to be scanned can be mounted, and the swivel bearing has a swivel axis extending normal to the scanning direction V.

The invention further relates to a method for carrying out three dimensional scanning of dental models in a scanning direction V along a Z-axis, in which method a whole jaw model to be scanned is mounted on a stage having a swivel axis extending normal to the scanning direction V, and the whole jaw model to be scanned is detected by a detector in a plurality of images and computation is performed by an evaluation unit for the purpose of creating a 3D-data set.

PRIOR ART

A scanning system for carrying out a 3D scan of dental models is disclosed in DE 10 2004 054 876 B3. This scanning system comprises an imaging device and a positioning system, which includes a panel that can be positioned relatively to the imaging device and to which the object to be scanned can be attached, and a base plate is provided that is stationary relative to the imaging device, and the displaceable panel contains a first set of locking means and the base plate is in the form of a locking panel and has a second set of locking means which interacts with the first set of locking means in such a manner that the displaceable panel can assume a plurality of specific positions relative to the locking panel and can be locked in the selected position.

EP 0 913 130 A2 discloses a scanning system for carrying out 3D scanning of whole jaw models, which scanning system comprises a clamping device for holding the dental model, and the clamping device can swivel about a swivel axis. The swivel axis is aligned parallel to a plane of the whole jaw model, i.e. to a turntable carrying the same.

It is an object of the present invention to configure and arrange a scanning system and to develop a scanning method in a manner that ensures more precise and rapid scanning of a whole jaw model.

SUMMARY OF THE INVENTION

According to the invention, the device is provided with a stage that is mounted such that it can rotate about the swivel axis relative to the base through an angular range $\delta$ of at least 150°, and the whole jaw model can be mounted such that the occlusal plane E is aligned parallel to the scanning direction V, and an axis of rotation of the whole jaw model extends coaxially with the swivel axis of the swivel bearing and normal to the occlusal plane E. The procedure used comprises the following steps: creating a first image of the dental model to be scanned at that angular position W1 of the swivel-type stage that is determined by the positioning means, swiveling the whole jaw model about its swivel axis extending normal to an occlusal plane E spanning a line-shaped mandibular arch through a swivel angle $\alpha$ to at least one other angular position W2 predefined by the positioning means, and creating another image and producing a 3D data set by evaluating the images created from at least two different, precisely predefined angular positions W1, W2. This makes it unnecessary to scan individual parts of the dental model for the purpose of creating a whole jaw data set, and enables the entire jaw model to be scanned as a whole. In particular, the outer buccal and labial tooth surfaces are detected from a substantially normal direction so that they can be scanned in an optimum manner, particularly with regard to the brackets disposed, or to be disposed, thereon for correcting the position of certain teeth. The swivel axis of the swivel bearing is preferably aligned normal to the scanning direction V so that the aforementioned outer tooth surfaces can be scanned in an optimum manner. Alternatively, the swivel axis might be arranged to deviate from this arrangement, but this would result in a wobbly rotational movement of the whole jaw model relative to the scanning direction, which in turn would involve the necessity for a sufficiently large image-detecting area. The swivel bearing advantageously comprises positioning means providing a plurality of predefined angular positions W1, W2 of the holding device, in the direction of rotation of the swivel bearing about the swivel axis. The use of a number of predefined angular positions such as W1, W2 minimizes the total number of images required to scan the whole jaw model, provided that the respective angular positions are adapted to suit the scanning window available.

Likewise, according to the invention, the stage can be mounted such that it can swivel about the swivel axis relatively to the base through an angular range $\delta$ of at least 150°, while the swivel bearing comprises positioning means providing a number of predefined angular positions W1, W2 of the holding device in the direction of rotation of the swivel bearing about the swivel axis. This variant likewise produces the aforementioned advantages.

Another advantage is that a detector having an optical axis can be provided which generates a measuring zone in a scanning direction V, wherein the optical axis and/or the scanning direction V are in parallel alignment, preferably in a vertical direction. The orientation and arrangement of the detector ensures optimum detection of the buccal, i.e. radially outer, surfaces of the teeth in the whole jaw model.

Furthermore, it is advantageous if the distance between the detector and the swivel bearing can be adjusted at least in the direction of the Z-axis. Depending on the depth of field of the measuring optics used, it is possible to adjust the distance between the detector and the swivel bearing or between the detector and the aforementioned outer tooth surfaces, in order to take into account the depth of field on the one hand and the various model sizes on the other.

In this context, it is advantageous if the detector can comprise telecentric optics giving an image detection zone having a length L, a width B and a depth of field T. In particular, the width B of the image detection zone determines the number of teeth that can be recorded at a time in any part of the whole jaw model and thus the number of images required to cover the entire jaw model. If the depth of field is sufficiently large or the whole jaw model is positioned suitably during the swiveling movement, all images can be created for the whole jaw model without the aforementioned adjustment of the distance between the detector and the swivel bearing.

Furthermore, it is advantageous if a measuring circle K oriented with respect to the mandibular arch and disposed coaxially with the axis of rotation is assigned to the whole jaw model such that a radial distance dr between an outer buccal tooth surface ZA and the measuring circle K is shorter than the depth of field T. The dental or mandibular arch itself represents an approximately semi-elliptical or semi-oval base form on which the teeth of the whole jaw model are located. According to the invention, a measuring circle K can be positioned over this given mandibular jaw in such a way that the outer buccal and labial tooth surfaces of the whole jaw model are located at the least possible distance or, more particularly, at a maximum distance from the positioned measuring circuit, which distance ensures uniform scanning of the whole jaw model taking into account the existing depth of field T. This ensures that when the whole jaw model is swiveled about the axis of rotation or swivel axis, the outer tooth surfaces to be imaged will always be located within the range of the depth of field T of the optics.

It is likewise advantageous if a rotary angle α between two angular positions W1, W2 can range from 20° to 40°. The size of the rotary angle α between two angular positions W1, W2 can be adapted, in particular, to the width of the available scanning window or image detection zone such that the least possible number of images is required for a comprehensive image of the whole jaw model.

It is also advantageous if a radian measure S on the measuring circle K be not larger than the width B of the image detection zone but larger than half the width B of the image detection zone. The rotary angle α should be such that adjacent image zones overlap in such a way that adjacent images can be oriented relatively to each other based on this overlap zone when the images are subsequently joined together.

Moreover, it is advantageous if the rotary angle α can be selected such that image zones D1, D2 recorded at adjacent angular positions have an overlap zone O of at least one tenth of the width B of the image detection zone. If the size of the overlap zone O is equal to one tenth of the width of the image detection zone, the aforementioned relative orientation of adjacent images is ensured. Furthermore, a sufficiently small number of total images is necessary to image the whole jaw model, i.e., all outer tooth surfaces.

It is further advantageous if an evaluation unit can be provided which computes a 3D data set on the basis of at least two images. Based on the computed 3D data set produced by the evaluation unit, rapid determination of the positions or orientation of the required brackets is possible.

In the method of the invention for carrying out three-dimensional scanning of dental models in a scanning direction V along a Z-axis, in which a whole jaw model is fixed on a stage having a swivel axis located in an X-Y plane and the whole jaw model to be scanned is detected by a detector in a plurality of images and an evaluation unit performs computation to create a 3D data set, a) a first image of the dental model to be scanned is produced at that angular position W1 of the swivel-type stage that is determined by positioning means,
b) the whole jaw model is swiveled about its swivel axis extending normal to an occlusal plane E spanning a line-shaped dental or mandibular arch through the swivel angle α to at least one other angular position W2 predefined by the positioning means, and another image is created, and
c) a three-dimensional data set is produced by evaluating the images produced from at least two different precisely defined angular positions W1, W2.

It is likewise advantageous if, for the purpose of positioning the whole jaw model, a measuring circle K having a center M and oriented with respect to the outer buccal tooth surfaces ZA can be positioned such that a radial distance dr between the measuring circle K and an outer buccal tooth surface ZA is not larger than the depth of field T of the detector.

It is further advantageous if the axis of rotation of the whole jaw model can be located in the center M, and the swivel axis of the swivel bearing is oriented coaxially with the axis of rotation.

In addition, it is advantageous if the distance between the detector and the swivel bearing and/or the measuring circle K can be adjusted at least for one angular position W1, W2 taking into account the depth of field T of the optics and the size of the whole jaw model.

Furthermore, it is advantageous if the angle α between the angular positions W1, W2 of the swivel bearing is known to the evaluation unit and the evaluation unit can join the images together allowing for an overlap of the image detection zones, as caused by the swivel angle α.

Finally, it is advantageous if the evaluation unit can compare the individual images with each other in an overlap zone O of the images in order to determine the positions of the images relative to each other, and if the individual images can be combined to form a common data set.

Exemplary embodiments of the invention are shown in the drawing.

BRIEF DESCRIPTION OF THE DRAWINGS

FIG. 1b is a side view of the illustration of FIG. 1a;

DETAILED DESCRIPTION OF THE PREFERRED EMBODIMENT

Figure 1A:
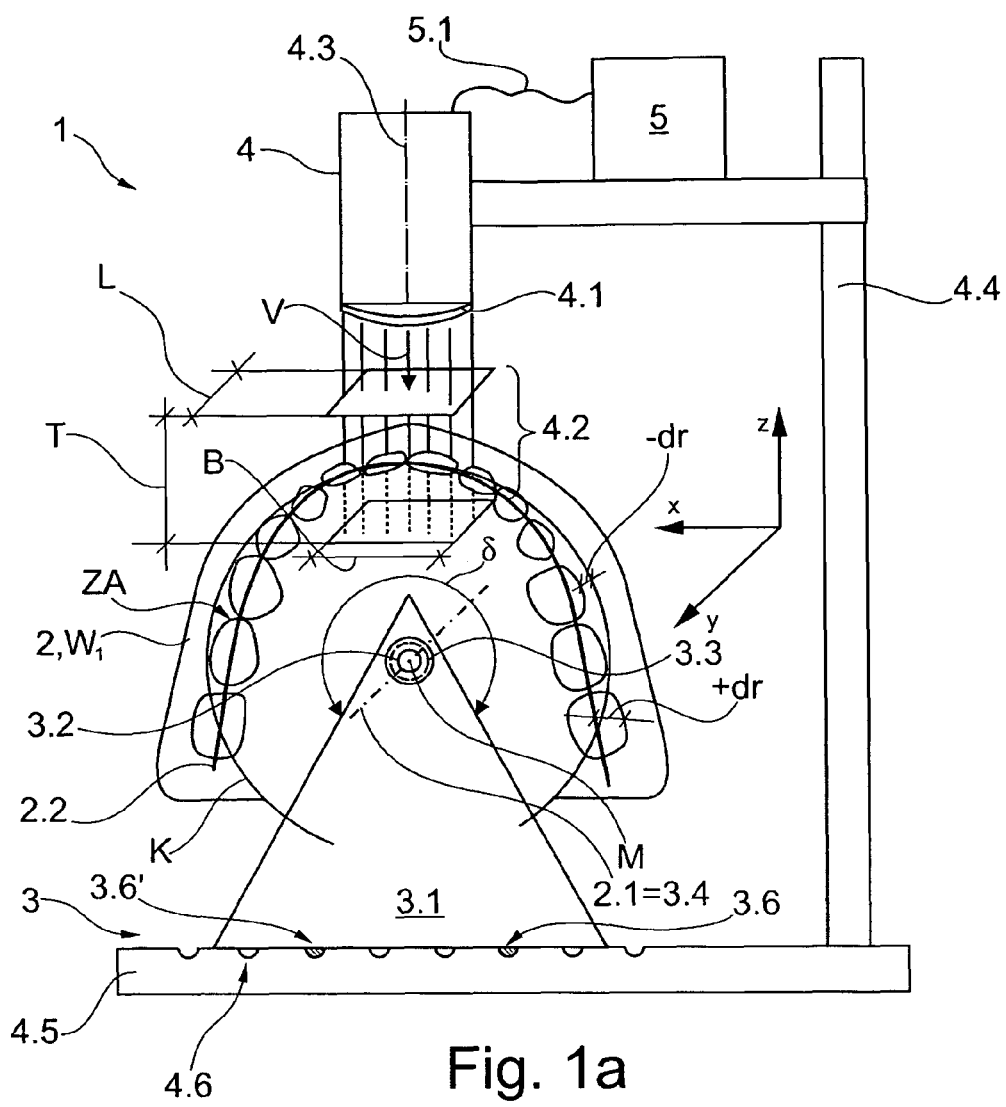
FIG. 1a is a diagrammatic illustration of the scanning system including the rotatably mounted whole jaw model.

A scanning system 1 shown in FIG. 1 comprises a holding device 3 that includes a base 3.1 having a rotatable stage 3.2. The stage 3.2 serves to accommodate a whole jaw model 2 and comprises a swivel bearing 3.3 with a swivel axis 3.4. The swivel axis 3.4 is aligned parallel to a Y-axis.

The base 3.1 with the stage 3.2 is disposed on a base plate 4.5 located in an X-Y plane. For the purpose of adjusting the relative position between the base 3.1 and the base plate 4.5, the base 3.1 comprises a plurality of notches 3.6, 3.6', which engage in appropriately disposed grooves 4.6 in the base plate 4.5. The grooves 4.6 are disposed at regular intervals such that the base 3.1 can be adjusted along an X-axis to the right and to the left to assume predefined positions relative to the base plate 4.5, as shown in FIG. 1a.

Figure 1B:
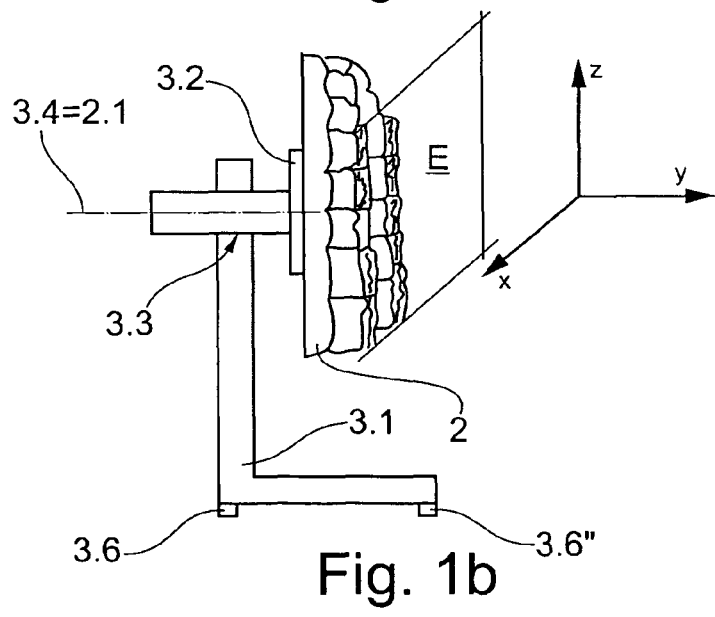

As seen in FIG. 1b, the base 3.1 comprises at least one other notch 3.6", which is disposed to the rear along a Y-axis to ensure static firmness of the base 3.1. For the purpose of scanning the whole jaw model 2 as shown in FIG. 1a, a detector 4 is provided which can be positioned on a column 4.4 directly above the whole jaw model 2, i.e., above the swivel axis 3.4. Gearing (not shown) on the column 4.4 makes it possible to adjust the distance between the detector 4 and the whole jaw model 2 along a Z-axis. The detector 4 is connected via a data line 5.1 to an evaluation unit 5 used for evaluating the detected image data. The detector 4 has an optical axis 4.3 extending parallel to the Z-axis and a scanning direction V aligned parallel to the optical axis 4.3. In this scanning direction V, the detector 4 generates an image detection zone 4.2 of width B, length L, and depth of field T. The detector 4 is disposed at a distance above the whole jaw model 2 in the axis Z such that the part of the whole jaw model 2 that is to be scanned is disposed within the image detection zone 4.2 defined above. For the purpose of positioning and aligning the whole jaw model 2, a measuring circle K, which is oriented according to a line-shaped dental or mandibular arch 2.2, is assigned to the whole jaw model 2. The aforementioned measuring circle K is positioned in relation to the mandibular arch 2.2 such that radial distances dr between the outer tooth surfaces ZA and the measuring circle K are as small as possible. As shown in FIG. 1a, the fifth tooth on the right is disposed at a distance (−dr) from the measuring circle K, while the seventh tooth on the right is disposed at a distance (+dr) from the measuring circle K. The diameter of the measuring circle K must be selected such that the aforementioned distances (−dr, +dr) of the measuring circle from the respective outer tooth surfaces ZA are disposed within the depth of field T of the detector 4, which ensures that the whole jaw model 2 is located within the depth of field T when the dental model is swiveled about the swivel axis 3.4. The adjustment of the distance between the detector 4 and the whole jaw model 2 along the Z axis is made possible by gearing (not shown) on the column 4.4 so that the measuring circle K or its center can be positioned such that the circle K is within the depth of field T, preferably mid-way along the depth of field T, taking into account the aforementioned distances (−dr, +dr). The whole jaw model 2 or the center M of the measuring circle K is disposed coaxially with the swivel axis 3.4 or coaxially with an axis of rotation 2.1 of the whole jaw model 2. As shown in FIG. 1a, the whole jaw model 2 is disposed in a rotational position W1 relative to the axis of rotation 2.1.

Figure 2:
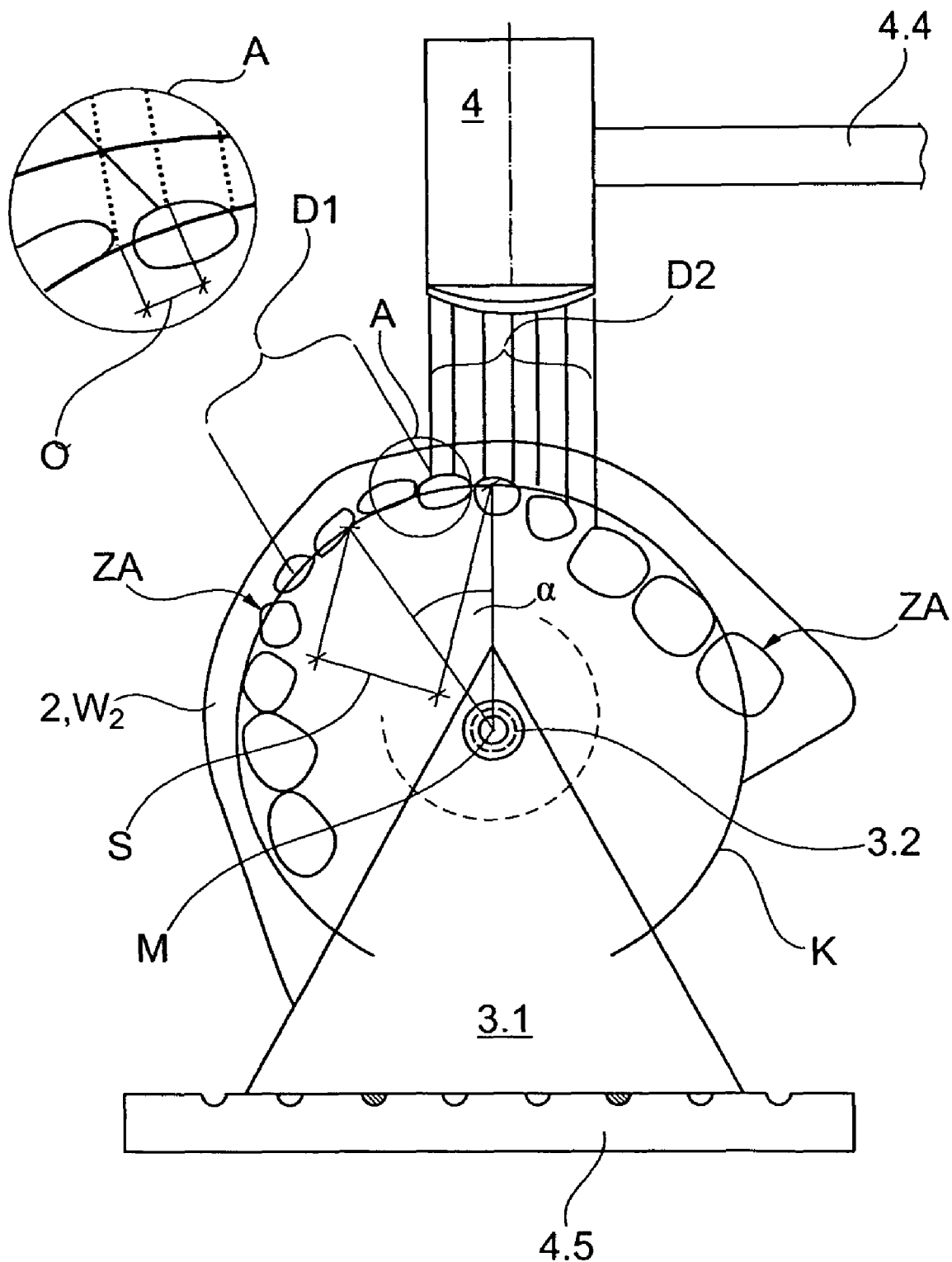
FIG. 2 shows the scanning system shown in FIG. 1 with the whole jaw model in a swiveled position.

In FIG. 2, the whole jaw model 2 is shown as swiveled through a swivel angle α toward the left to a position W2. By means of the detector 4, i.e., the image detection zone 4.2, an image zone D2 over the adjacent teeth of the whole jaw model 2, i.e., the outer surfaces ZA thereof is recorded which differs from the image zone D1 recorded according to FIG. 1a. The two image zones D1 and D2 have an overlap zone O, as shown in the enlarged portion of the detail A. The overlap zone O results from the ratio of the width of the image area to a radian measure S derived from the swivel angle α resulting from swiveling the whole jaw model 2 from position W1 to position W2.

The axis of rotation 2.1 of the whole jaw model 2 and the swivel axis 3.4 are disposed coaxially with each other and the center M of the measuring circle K is likewise located in the two aforementioned axes. The distance dr between the measuring circle K and the detector 4 is thus constant. The outer buccal and labial tooth surfaces ZA are disposed at a given distance dr, as shown in FIG. 1a, from the measuring circle K, which ensures that all of the outer tooth surfaces ZA to be recorded are located within the depth of field T when the whole jaw model is rotated through an angular range 6, shown in FIG. 1a, taking into account the available depth of field T of the detector 4.

In FIG. 1b, occlusal surfaces of the various teeth of the whole jaw model 2 are set to an occlusal plane E, which, according to the invention, is normal to the swivel axis 3.4 of the swivel bearing 3.3 and parallel to the scanning direction V.

REFERENCE NUMERALS 1 scanning system
2 dental model, whole jaw model
2.1 axis of rotation
2.2 dental/mandibular arch
3 holding device
3.1 base
3.2 stage
3.3 swivel bearing
3.4 swivel axis
3.6 notch
3.6' notch
3.6" notch
4 detector
4.1 optics
4.2 image detection zone
4.3 optical axis
4.4 column
4.5 base plate
4.6 snap-in grooves
5 evaluation unit
5.1 data line
α swivel angle
δ angular range
A image segment
B width of the image detection zone
D1 image zone
D2 image zone
dr distance
E occlusal plane
K measuring circle
L length of the image detection zone
M center
O overlap region
S radian measure
T depth of field
V scanning direction
W1 angular position
W2 angular position
X direction
Y direction
Z direction
ZA outer tooth surfaces

The invention claimed is:

1. A scanning system (1) for 3D scanning of dental models (2) in a vertical scanning direction V, comprising a holding device (3) for a whole jaw model (2), a base (3.1), a swivel bearing (3.3) on a swivel axis (3.4) normal to the scanning direction V, and a stage (3.2) mounted for rotation on the swivel bearing (3.3) relatively to said base (3.1) and on which the dental model to be scanned (2) can be mounted, wherein said stage (3.2) is mounted for rotation relatively to said base (3.1) through an angular range σ of at least 150° about said swivel axis (3.4), and the whole jaw model (2) can be mounted such that said occlusal plane E is aligned parallel to said scanning direction V, an axis of rotation (2.1) of said whole jaw model (2) is coaxial with the swivel axis (3.4) of said swivel bearing (3.3) and is normal to said occlusal plane E, wherein a measuring circle K which is coaxial with the axis of rotation (2.1) in alignment with said mandibular arch (2.2) is positioned with respect to said whole jaw model (2) such that a radial distance dr between an outer buccal tooth surface ZA and said measuring circle K is shorter than the depth of field T.

2. The scanning system (1) according to claim 1, wherein said swivel bearing (3.3) has positioning means which provide a plurality of predefined angular positions W1, W2 of said holding device (3) in the direction of rotation of said swivel bearing (3.3) about said swivel axis (3.4).

3. The scanning system (1) according to claim 2, including a detector (4) having an optical axis (4.3) which generates a measuring zone in the scanning direction V, and the optical axis (4.3) and/or the scanning direction V are aligned in parallel.

4. The scanning system (1) according to claim 3, wherein a distance between said detector (4) and said swivel bearing (3.3) is adjustable at least along a vertical Z axis.

5. The scanning system (1) according to claim 4, wherein said detector (4) comprises telecentric optics (4.1) showing an image detection zone (4.2) having a length L, a width B, and a depth of field T.

6. The scanning system (1) according to claim 1, wherein a swivel angle α between two angular positions W1, W2 has a magnitude between 20° and 40°.

7. The scanning system (1) according to claim 6, wherein a radian measure S of said measuring circuit K corresponding to said swivel angle α has a magnitude not larger than the width B of said image detection zone (4.2) and is larger than half the width B of said image detection zone (4.2).

8. The scanning system (1) according to claim 7, wherein said swivel angle α is selected such that image segments D1, D2 recorded in adjacent angular positions W1, W2 have an overlap zone O having a magnitude equal to at least one tenth of the width B of said image detection zone (4.2).

9. The scanning system (1) according to claim 6, wherein an evaluation unit (5) is provided which performs computation of a 3D data set on the basis of at least two images.

10. A method for carrying out 3D scanning of dental models (2) in a scanning direction V along a Z axis, in which a whole jaw model to be scanned (2) is attached to a stage (3.2) having a swivel axis (3.4) extending normal to said scanning direction V and the whole jaw model to be scanned (2) is detected by a detector (4) in a plurality of images and, for the purpose of creating a 3D data set of the dental model (2), computation is carried out by an evaluation unit (5), comprising the following steps:
  a) positioning said whole jaw model (2) by measuring circle K oriented with respect to the outer buccal tooth surfaces ZA and having a center M is positioned such that a radial distance dr between said measuring circle K and an outer buccal tooth surface ZA is not greater than the depth of field T of said detector (4), wherein said axis of rotation (2.1) of said whole jaw model (2) coincides with the center M, and said swivel axis (3.4) of said swivel bearing (3.3) is aligned coaxially with said axis of rotation (2.1),
  b) creating a first image of the tooth model (2) from a vertical scanning direction V to be scanned at an angular position W1 of said rotatable stage (3.2), as set by positioning means,
  c) swiveling the whole jaw model (2) about said swivel axis (3.4) of said whole jaw model (2) aligned normal to an occlusal plane E spanning a line-shaped mandibular arch (2.2) through a swivel angle α to at least one further angular position W2 specified by said positioning means and creating another image, and
  d) creating a 3D data set by evaluating the images created at at least two different, precisely defined angular positions W1, W2.

11. The method according to claim 10, wherein the distance between said detector (4) and the swivel bearing (3.3) and/or measuring circle K is adjusted for at least one angular position W1, W2 taking into consideration the depth of field T of the optical system (4.1) and taking into consideration the size of said whole jaw model (2).

12. The method according to claim 11, wherein the angle α between the angular positions W1, W2 of said swivel bearing (3.3) is known to said evaluation unit (5) and said evaluation unit (5) joins said images together taking into consideration an overlap of said image detection zones (4.2) resulting from said swivel angle α.

13. The method according to claim 11, wherein in order to determine the positions of the images relative to each other, said evaluation unit (5) compares the individual images with each other in an overlap zone O of said images.

14. The method according to claim 13, wherein said individual images are combined to form a common data set.

* * * * *